United States Patent [19]
Collier et al.

[11] Patent Number: 6,125,685
[45] Date of Patent: Oct. 3, 2000

[54] APPARATUS AND METHOD FOR THE EVALUATION OF ASPHALT MIXES

[75] Inventors: Rebecca E. Collier, Madison, Iowa; Mark L. Kuss, Lowell, Ark.

[73] Assignee: The Board of Trustees of the University of Arkansas, Little Rock, Ak.

[21] Appl. No.: 09/163,945

[22] Filed: Sep. 30, 1998

Related U.S. Application Data

[60] Provisional application No. 60/061,403, Sep. 30, 1997.

[51] Int. Cl.$^7$ .............................. E01C 23/01; G01L 5/00; G01M 19/00
[52] U.S. Cl. ............................ 73/7; 73/866; 73/8; 73/146
[58] Field of Search .................................. 73/7, 8, 81, 85, 73/800, 148

[56] References Cited

U.S. PATENT DOCUMENTS

| | | |
|---|---|---|
| 2,287,148 | 6/1942 | Taber . |
| 4,887,463 | 12/1989 | Wood . |
| 4,938,055 | 7/1990 | Tsuda . |
| 5,641,901 | 6/1997 | Powell . |
| 5,987,961 | 11/1999 | Harris et al. .............................. 73/7 X |

*Primary Examiner*—Daniel S. Larkin
*Attorney, Agent, or Firm*—J. M. (Mark) Gilbreth; Gilbreth & Associates, P.C.

[57] ABSTRACT

The present invention provides and apparatus and method for analyzing the rutting and stripping characteristics of hot mix asphalt concrete samples. The apparatus of the invention measures the vertical penetration of a wheel rolling in a reciprocating motion across the surface of a compacted asphalt mix specimen. The apparatus incorporates precise environmental control and includes features for testing two or more samples simultaneously under wet or dry conditions or a combination of wet and dry conditions.

11 Claims, 5 Drawing Sheets

APPARATUS AND METHOD FOR THE EVALUATION OF ASPHALT MIXES

RELATED APPLICATION DATA

This application claims priority of U.S. provisional application, Ser. No. 60/061,403 filed Sep. 30, 1997.

BACKGROUND OF THE INVENTION

1. Field of the Invention

The present invention relates to an apparatus and method for evaluating samples. In another aspect, the present invention relates to an apparatus and method for evaluating asphalt samples. In even another aspect, the present invention relates to a wheel tracking apparatus and method to evaluate the rutting and stripping potential of hot mix asphalt concrete samples. In still another aspect, the present invention relates to a wheel tracking apparatus and method to evaluate hot mix asphalt concrete samples where two or more samples may be tested simultaneously under wet, dry, or a combination of wet and dry conditions.

2. Description of the Related Art

The asphalt-concrete used as a major component of an asphalt pavement generally consist of a mixture of about 5% asphalt and 95% rock aggregate by weight. The pavement material is formulated by mixing the two ingredients in a heated and rotating drum. The material is then extruded from specially designed machines onto a prepared roadway base. The pavement surface is finished by using rollers to compact and consolidate the mix and prepare the surface for traffic.

Rutting and stripping are two major distresses which occur in pavements constructed of hot mix asphalt concrete (HMAC). Rutting is the formation of depressions in the pavement in the direction of traffic flow under the influence of a moving wheel load. Stripping is the physical separation of asphalt cement from aggregate.

Rutting is caused primarily by repetitive shear deformations under traffic loading, although mixture densification (volume change) plays a minor role. Factors which influence the amount of rutting include: wheel load magnitude; tire pressure; traffic volume, environmental conditions; subgrade stability; and HMAC mixture properties, such as aggregate type, gradation, asphalt content, and asphalt binder type.

Stripping is the failure of the adhesion between the aggregate and asphalt cement binder in HMAC. Stripping occurs when water gets between the asphalt binder and the aggregate surface, and/or when water interacts with the asphalt binder and reduces its cohesive properties. Factors that influence the occurrence and severity of stripping include physical and chemical properties of both the aggregate and asphalt cement and the environment in which the pavement exists.

A number of test methods have been devised in attempts to evaluate and/or predict these two failure characteristics. The methods most commonly used to predict rutting using laboratory test mixtures include uniaxial and creep tests; uniaxial and triaxial repeated load tests; triaxial dynamic tests; diametral tests (creep and repeated load); hollow cylinder tests (combined axial and torsional loading); and simple shear tests (unconfined and confined).

Laboratory tests to gauge moisture damage in HMAC generally include: visual stripping evaluation of a "conditioned" uncompacted mix; or evaluating a compacted mixture property (i.e. stiffness, strength) in terms of a ratio of "conditioned" to "unconditioned".

Although these methods are used by many transportation agencies and asphalt pavement technologists, there is general agreement that none of these tests consistently gives results that correlate well with the occurrence of rutting and/or stripping in the field. None of these tests types have established a consistent record of accurately predicting moisture-susceptible mixtures. Consequently, pavement engineers are seeking better and more reliable testing methods.

More recently, "wheel-tracking" tests, in which a loaded wheel repeatedly travels across an HMAC specimen to simulate the action of traffic, have been utilized to predict the rutting and/or stripping potential of the sample. One wheel-tracking test uses the Hamburg wheel tracking device, developed by Helmut-Wind, Inc. of Hamburg, Germany. In the standard Hamburg test, two HMAC specimens are submerged in water maintained at 50° C. (122° F.) and subjected to repeated passes of a steel wheel loaded to 703N (158 lbf). The test is performed to a maximum of 20,000 passes or until a specimen deformation of 20 mm (0.79 in) is recorded.

From the results of the Hamburg test, it may be possible to identify both a "rutting" and a "stripping" phenomenon. However, questions arise concerning the interrelationship of the two failure mechanisms, i.e., the effect on the magnitude of the creep slope in a Hamburg test by the presence (or absence) of subsequent stripping. In other words, are submerged specimen tests generally applicable for evaluating "rutting" or more specifically, are "rutting" results from a standard Hamburg test affected by the fact the samples are submerged?

Therefore, there is a need in the art for an improved apparatus and method for the evaluation of samples.

There is another need in the art for an apparatus and method for the evaluation of HMAC samples that does not suffer from the limitations of the prior art.

There is even another need in the art for an apparatus and method for the evaluation of HMAC samples that consistently give results that correlate well with the occurrence of rutting and/or stripping in the field.

There is still another need in the art for an apparatus and method for the evaluation of HMAC samples that can determine the interrelationship of the rutting and stripping phenomenon in the wheel-tracking test.

These and other needs of the present invention will become apparent to those of skill in the art upon review of the specification, including its drawings and claims.

SUMMARY OF THE INVENTION

It is an object of the present invention to provide for an apparatus and method for the evaluation of samples.

It is another object of the present invention to provide for an apparatus and method for the evaluation of HMAC samples that does not suffer from the limitations of the prior art.

It is even another object of this invention to provide for an apparatus and method for the evaluation of HMAC samples that consistently give results that correlate well with the occurrence of rutting and/or stripping in the field.

It is still another object of this invention to provide for an apparatus and method for the evaluation of HMAC samples that can determine the interrelationship of the rutting and stripping phenomenon in the wheel-tracking test.

These and other objects of the present invention will become apparent to those of skill in the art upon review of this specification, including its drawings and claims.

According to one embodiment of the present invention, there is provided an apparatus for analyzing at least two samples. The apparatus generally includes a frame supporting sample containers. A first sample container is designed to maintain a sample in a dry state and a second sample container is designed to maintain a second sample in either a dry state or submerged in a liquid. The apparatus also includes a reciprocating member for simultaneously contacting a first and second sample and a sensor for measuring the penetration of the reciprocating member into the surface of the first and second sample.

According to another embodiment of the present invention, there is provided a method for analyzing a sample. The method generally includes: placing a first sample into a first sample container and maintaining the first sample dry; placing a second sample into a second sample container and maintaining the second sample dry or submerged in a liquid; simultaneously contacting the first and second test samples with a reciprocating member; and measuring the depth at which the reciprocating member penetrates the first and second samples.

These and other embodiments of the present invention will become apparent to those of skill in the art upon review of this specification, including its drawings and claims.

DETAILED DESCRIPTION OF THE INVENTION

The present invention shall now be described by reference to FIGS. 1–7 in which like reference numbers throughout the figures refer to like members.

Figure 1:
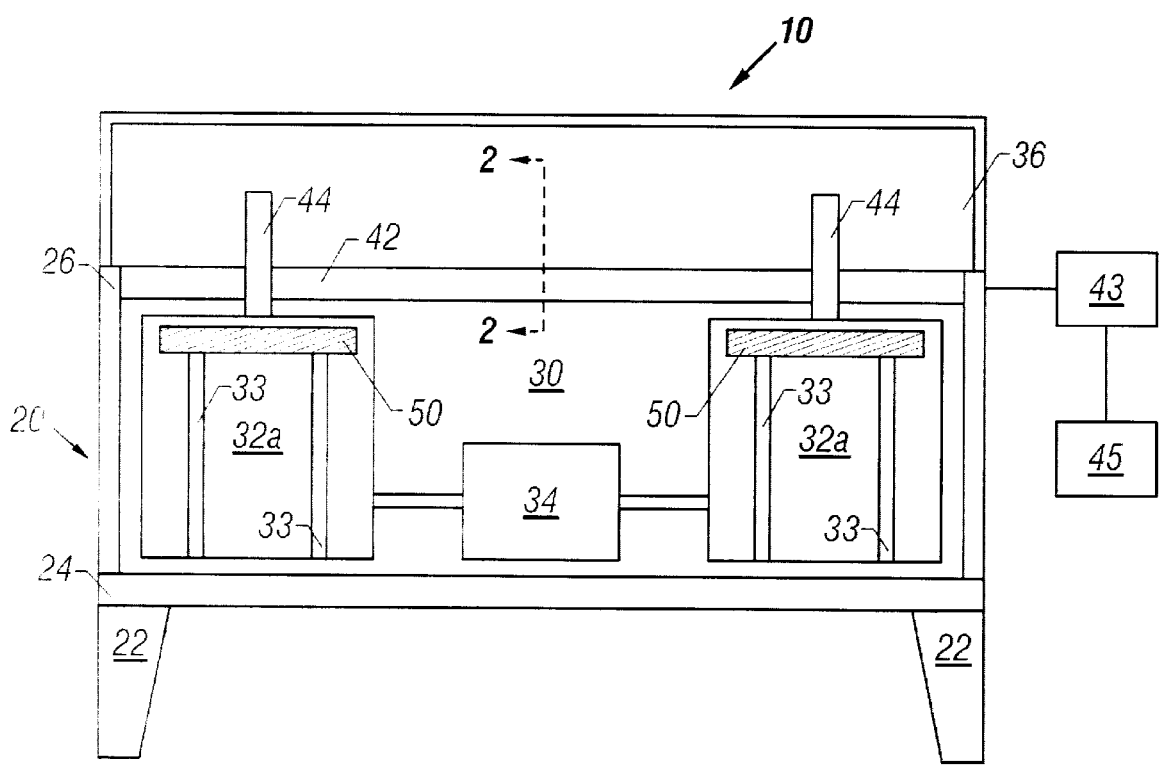
FIG. 1 Is a front view of the wheel tracking device of the present invention.

Referring first to FIG. 1. There is shown a front view of asphalt evaluator 10, which generally includes a structural frame 20 having lower cross beams 24, upper cross beams 26, and leg supports 22. Frame 20 including cross beams 26 and leg supports 22 may be constructed out of any materials suitable to provide structural integrity to support the evaluator 10. Non-limiting examples of suitable materials for frame 20 include steel or aluminum.

The lower set of beams 24 of frame 20 supports the bottom section of test chamber 30, which in the embodiment shown includes at least two tanks 32a and 32b which are designed to hold a fluid for wet testing conditions. While the embodiment shown in FIG. 1 includes two tanks, it is understood that test chamber 30 may comprise one or more tanks. It is noted that duplicate or multiple samples may be run with two or more tanks.

The temperature of water located within tanks 32a and 32b is controlled using any suitable external or internal temperature control unit 34. It is noted that temperature controllers are well known in the art, and it is believed that any suitable commercially available temperature control unit may be utilized as temperature control unit 34. It is also noted that the particular location of temperature control unit 34 is not critical. For example, unit 34 may be located within test chamber 30 as shown in the figures or located next to evaluator 10, or in any other suitable location.

The air temperature within chamber 30 is controlled using a temperature controller placed externally or contained within the outer walls of the testing apparatus 10. Again, it is noted that temperature controllers are well known in the art, and it is believed that any suitable commercially available temperature control unit may be utilized to control the air temperature. It is also noted that the particular location of the air temperature control unit is not critical.

Generally, the air temperature and water bath temperature are both maintained at the necessary temperatures for conducting the tests, which will be determined by the particular test procedure selected and the type of sample. It is understood that the air and water bath temperatures are test parameters which may be set at any temperatures depending on the test conditions desired. Obviously, the temperature must not be so low as to freeze the liquid bath nor so high as to boil it. The temperatures must also be selected to avoid undue degradation of the samples. As a non-limiting example, air temperature and water bath temperature test parameters may be maintained in the range of about 1° C. to about 60° C. More preferably, the temperatures are between about 45° C. to about 55° C.; and most preferably, between about 49° C. to about 52° C.

Frame 20 optionally supports cover 36 which when closed operates to help maintain the desired environmental test conditions throughout test chamber 30.

Tanks 32a and 32b may be or may not be filled with water or other liquid. This feature allows duplicate samples 50 to be simultaneously tested under submerged conditions, dry conditions, or both submerged and dry conditions.

The upper cross beams 26 of frame 20 supports a set of drive bars 42 which support two or more testing wheels 44. Drive bars 42 may driven via variable speed gear drive 43 connected to a drive motor 45 which provides the power to cause the wheels 44 to oscillate back and forth over the asphalt pavement samples 50. However, it is understood that any suitable means known may be utilized to cause wheels 44 to reciprocate. For a non-limiting example, a ball screw drive may be used.

Figure 2:
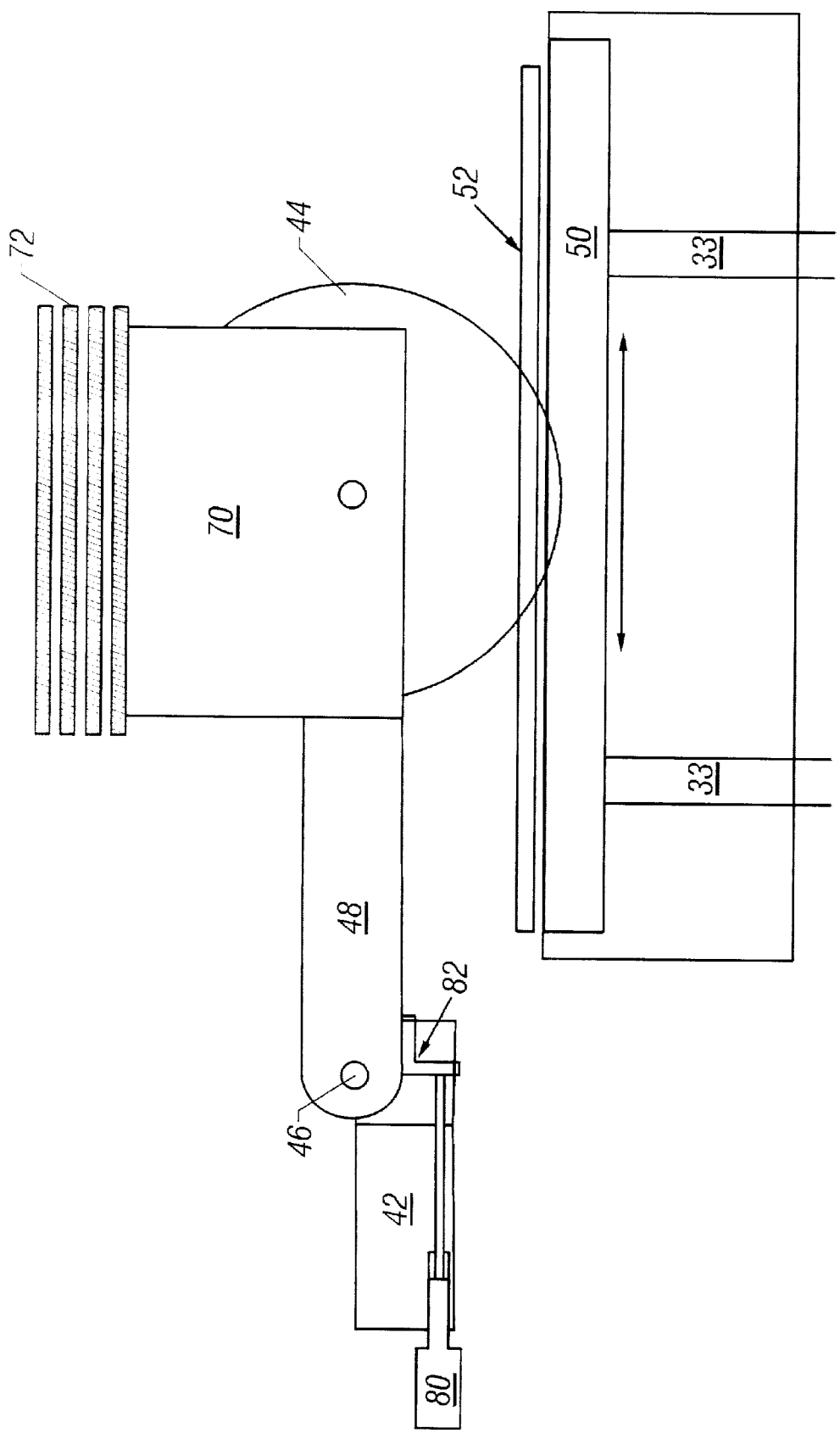
FIG. 2 Is a side view of the testing wheel of the present invention.

Referring now additionally to FIG. 2, which is a cross sectional view of FIG. 1, taken along line 2—2, testing wheels 44 pivot at a point 46 near the front of drive bar 42. Wheels 44 are connected to pivot point 46 by straight or curved support arms 48. Wheels 44 may be in direct contact with the asphalt pavement sample 50, or one or more intermediate layers of flexible material 52 may be placed between the testing wheels 44 and the sample 50. The pivot 46 and connecting support arm 48 allow the wheels 44 to be lifted for placement of a test section of asphalt pavement 50 into either or both of two containers 32a and 32b. While the sample 50 is shown supported within tank 32 by vertical columns 33, any suitable sample support may be utilized.

Testing wheels 44 are operated for a suitable number of cycles for the sample being tested. It is understood that the number of cycles is a test parameter which may be set at any number of cycles depending on the test conditions desired. As a non-limiting example, testing wheels 44 typically operate for about 5000 cycles to about 80,000 cycles, more preferably between about 20,000 cycles to about 40,000 cycles.

Testing wheels 44 are operated at a suitable speed for the sample being tested. It is understood that the speed of the testing wheels 44 is a test parameter which may be set at any number depending on the test conditions desired. As a non-limiting example, testing wheels 44 typically operate at a speed of between about 50 cycles/hour to about 4000 cycles/hour.

Testing wheels 44 operate for a stroke distance preferably between about one to about twenty-four inches, more preferably for a stroke distance of between about four to about fourteen inches. It is understood that the stroke distance of testing wheels 44 is a test parameter which may be set at any length depending on the test conditions desired.

Testing wheels 44 may be of any shape suitable to perform a desired test or evaluation on the HMAC sample. As non-limiting examples, testing wheels 44 may be symmetrical, asymmetrical, rounded, oval or v-grooved, or combinations thereof. Preferably, wheels 44 are round. In addition, testing wheels 44 may be constructed of any material desired suitable for performing the desired tests. As non-limiting examples, testing wheels 44 may comprise metal, thermoplastic, thermoset, elastomeric, or ceramics. Preferably, wheels 44 are steel or rubber (solid or pneumatic), most preferably, steel.

The wheels 44 may directly contact the surface of the sample 50 directly or optionally indirectly through one or more intermediate layers of flexible material 52 which may be placed between the wheel 44 and the sample 50.

A load table 70 is attached to the wheel support arm 48 to allow placement of one or more weights 72 which supply the pressure that is in turn applied to the test sample 50. While weights 72 are shown in FIG. 2 to be square plates, it is understood that weights 72 may of any size and shape. It is also understood that a suitable load may be applied to sample 50 via static weights 72 as shown in FIG. 2 or provided via pneumatic pressure, or other type of loading.

The wheel load is generally selected according to the testing procedure utilized and the type of sample being tested. It is understood that the wheel load is a test parameter which may be set at any amount depending on the test conditions desired. For example, in many cases, the wheel load is preferably between about 55 lbs and about 250 lbs, and more preferably between about 100 lbs to about 200 lbs, and most preferably between about 140 lbs to about 160 lbs.

A Linear Variable Displacement Transducer (LVDT) 80 or other suitable measuring device, is placed on or made an integral part of drive bar 42. LVDT 80 monitors the depth to which the load wheels 44 penetrate or wear into the sample 50 while the wheel is in motion. Reaction block 82 attached to the wheel pivot arm 48 measures the penetration of wheel 44 into the sample 50 in relation to the surface of the fixed sample 50.

Data, reported by response of the LVDT 80 to the movement of reaction block 82 relative to its original location, are recorded by computer or other commercially available data acquisition devices. The rate of data acquisition will depend upon the type of equipment utilized and the sample parameters. Generally, any rate of data acquisition may be utilized. As a non-limiting example, the rate of data acquisition may be between 1 to about 1000 data points per pass of wheel 44, preferably between about 200 to about 400 data points per pass.

EXAMPLE

The following example is provided merely to illustrate the present invention, and is not intended to limit the scope of the claims.

Test Setup

Testing was conducted on a test apparatus of the present invention substantially as shown in FIGS. 1 and 2.

Specimens were tested at 25° C., as opposed to the normal testing temperature for Hamburg-type tracking tests of 50° C. A steel wheel loaded to 681 N (153 lbf) was used for specimen tracking. The test was performed for a minimum of 100,000 passes of the wheel.

HMAC Specimens

Specimens from three field sites were tested. Slabs measuring approximately 610 mm (24 in.) square were cut from existing pavements to the full depth of the asphalt concrete. The slabs were taken to the laboratory for test preparation. The sawed specimen size was approximately 152 mm (6 in.) by 279 mm (11 in.) by compacted thickness. The mixes included:

fiber-reinforced asphalt concrete; the gradation conforms to a "Type 2" surface course as defined by the Arkansas Highway and Transportation Department (AHTD). The fibers are polypropylene, and the asphalt cement grade is AC-30. The mix represents an overlay of an existing asphalt concrete pavement on U.S. 71 south of Fayetteville, Ark. At the time of sampling, the pavement had been open to traffic for about six months. In-place air voids averaged about five percent;

dense-graded asphalt concrete; the gradation conforms to a "Heavy Traffic" mix (surface and binder) as defined by AHTD. The specimens consisted of both the surface and binder courses of an HMAC overlay of an existing jointed reinforced concrete pavement (JRCP). The site is located on I-30 near Texarkana, Ark. At the time of sampling, the pavement had not yet been open to traffic. In-place air voids averaged about seven percent;

Superpave mix; the gradation conforms to Superpave specifications for a 12.5 mm (surface) and 25 mm (binder) mix. The specimens consisted of both the surface and binder courses of an HMAC overlay of an existing JRCP pavement. The site is located on I-30 near Texarkana, Ark. At the time of sampling, the pavement had not been open to traffic. In-place air voids averaged about seven percent.

Results and Discussion

Figure 3:
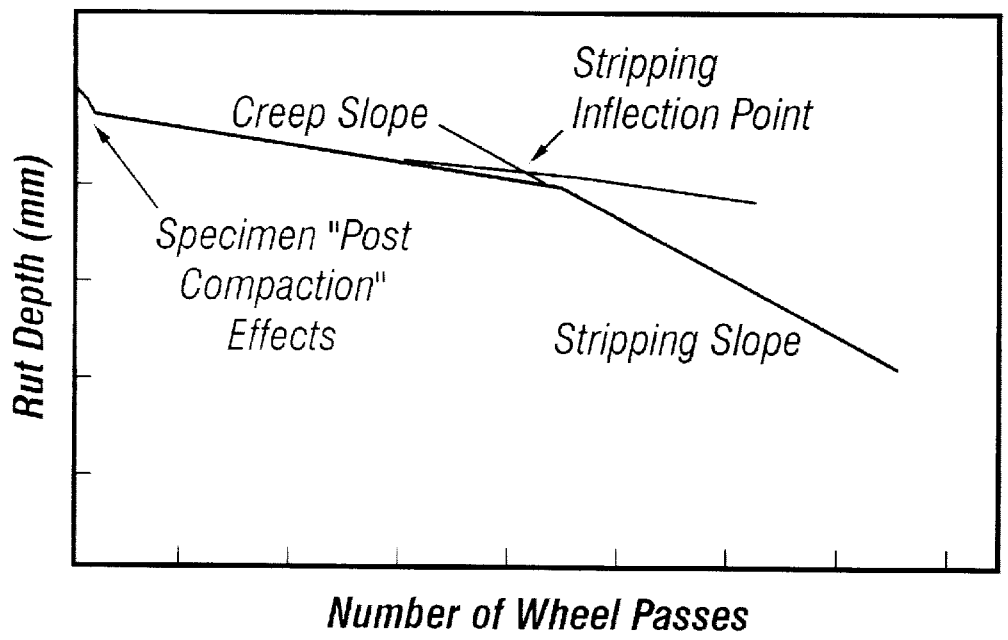
FIG. 3 Is a graphical representation of an Idealized Hamburg Wheel-Tracking Test Result showing Rut Depth v. Number of Wheel Passes.
Figure 4:
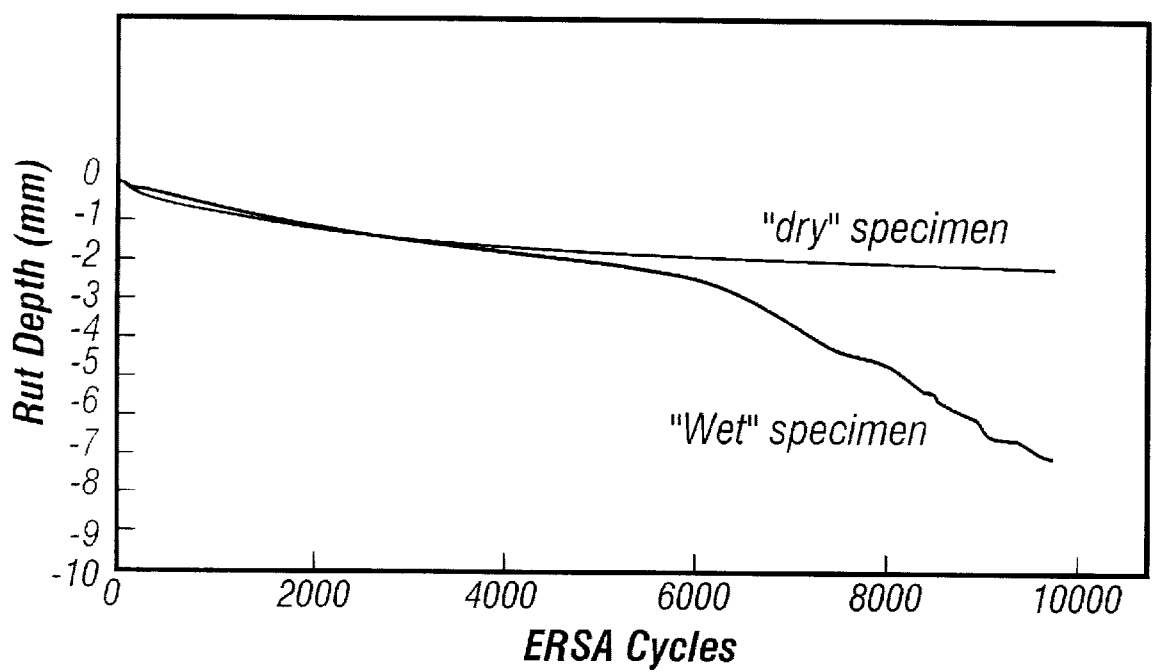
FIG. 4 Is a graphical representation of Rut Depth v. Cycles for Fiber-Reinforced HMAC.
Figure 5:
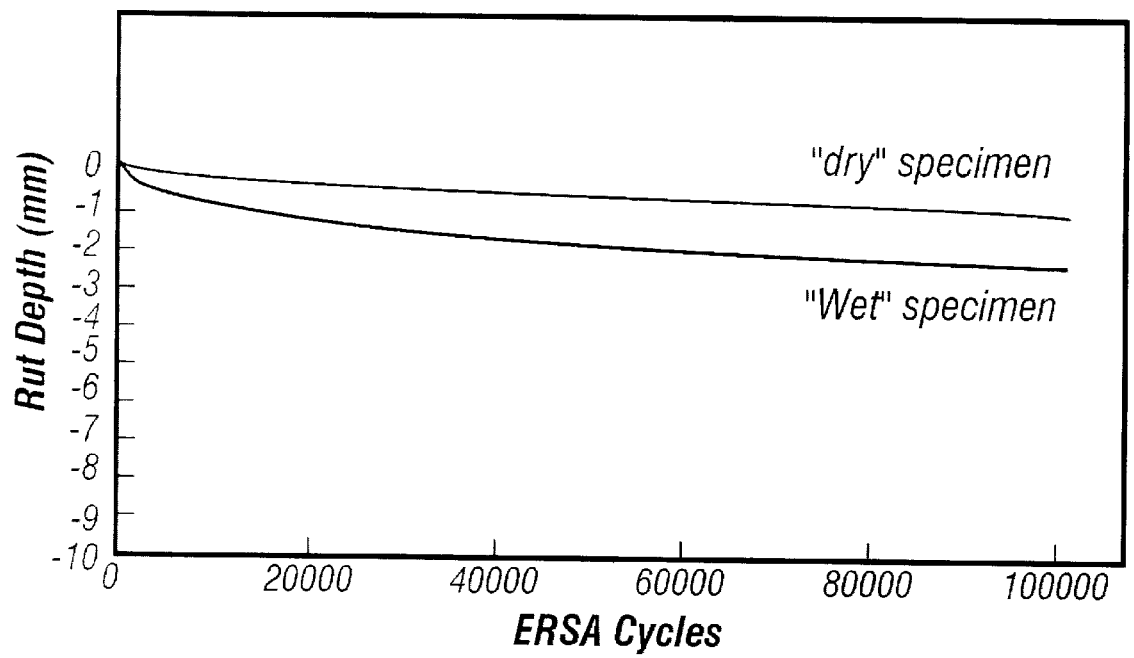
FIG. 5 Is a graphical representation of Rut Depth v. Cycles for Dense Graded HMAC.
Figure 6:
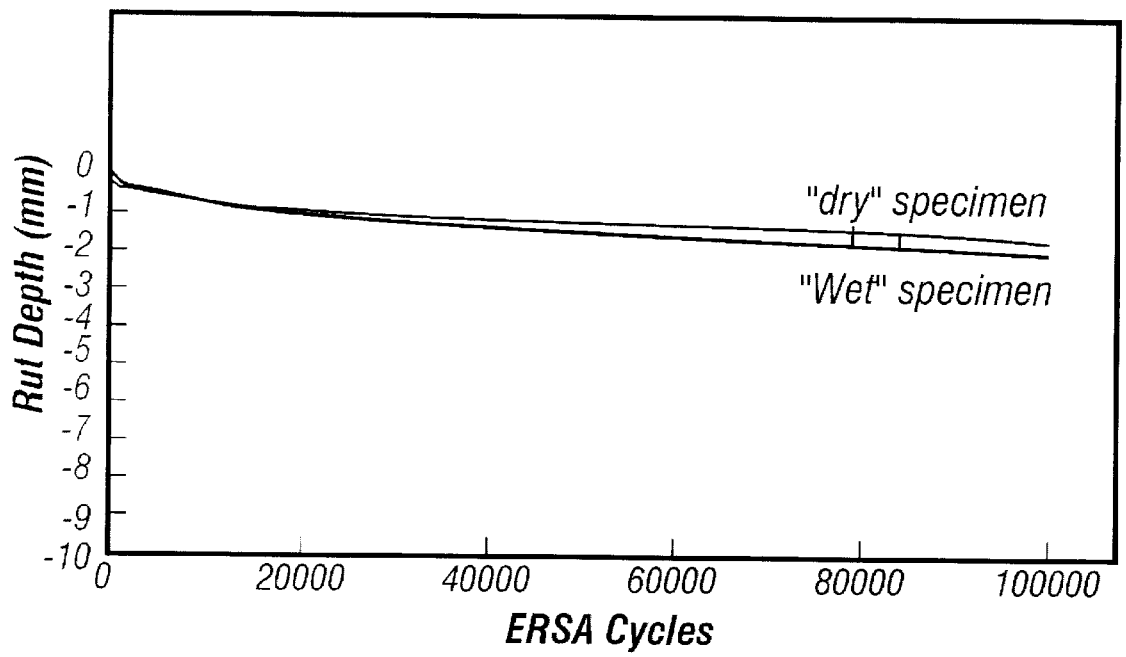
FIG. 6 Is a graphical representation of Rut Depth v. Cycles for Superpave Mix, Specimen 1.
Figure 7:
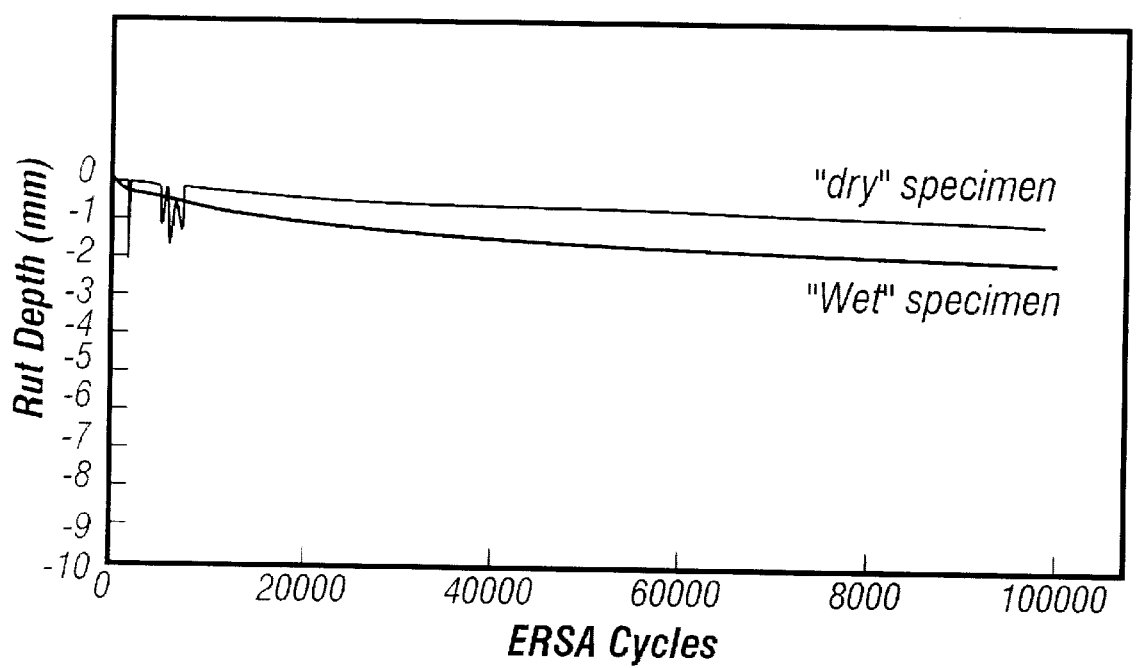
FIG. 7 Is a graphical representation of Rut Depth v. Cycles for Superpave Mix, Specimen 2.

FIGS. 4–7 show the results from the preliminary testing. FIG. 3 is a graphical representation of an Idealized Hamburg Wheel-Tracking Test Result showing Rut Depth v. Number of Wheel Passes. FIG. 4 is a graphical representation of Rut Depth v. Cycles for Fiber-Reinforced HMAC. FIG. 5 is a graphical representation of Rut Depth v. Cycles for Dense Graded HMAC. FIG. 6 is a graphical representation of Rut Depth v. Cycles for Superpave Mix, Specimen 1, and FIG. 7 is a graphical representation of Rut Depth v. Cycles for Superpave Mix, Specimen 2.

The first observation from the results is that none of the mixes tested would be considered rutting nor stripping susceptible with respect to common Hamburg-type wheel tracking criteria (e.g. the city of Hamburg requires a test specimen to exhibit less than 4 mm rut depth after 20,000 passes). However, it is noted that the test temperature for the results shown in FIGS. 4–7 is considerably less than that for a standard Hamburg test.

The primary interest in the results shown is the comparison of the "wet" specimen curves to the "dry" specimen curves. In this regard, FIG. 4, representing the fiber-reinforced asphalt concrete, yields some interesting observations. The wet specimen curve exhibits "classic" Hamburg-type wheel tracking behavior, with fairly well-defined creep and stripping slopes and stripping inflection point. The dry specimen curve shows a creep slope very similar to that of the wet specimen; only at the onset of stripping (around 50,000 cycles) do the curves visibly diverge.

FIGS. 5–7 show mixes that do not appear to be stripping susceptible, that is, no stripping slope or inflection points are evident. The creep slopes (wet and dry) for each set of specimens appear to be similar, the primary difference being the amount of post compaction deformation exhibited by the individual specimens.

A close inspection of the curves in FIGS. 4–7 in the region normally considered in Hamburg-type testing (less than 20,000 passes), however, reveals some difference in the creep slopes between wet and dry specimens. For purposes of comparison, the creep slop is calculated for the region of the curve between 10,000 and 20,000 passes. Table 1 lists the creep slope for each of the curves, wet and dry, shown in FIGS. 4–7. Also shown in Table 1 is the corresponding rut depth accumulation over the specified range of wheel passes.

TABLE 1

Creep Slope for Mixes Tested

| HMAC Specimen | | Creep Slope[a] (rut depth, mm) | | |
| --- | --- | --- | --- | --- |
| No. | Type | Wet | Dry | Dry/Wet Ratio |
| Fiber2b | Fiber-reinforced | 16560 (0.57) | 30134 (0.32) | 1.8 (0.56) |
| Texark2b | Dense-graded HT | 25650 (0.39) | 61986 (0.16) | 2.4 (0.41) |
| Texark1b | Superpave | 26955 (0.37) | 46326 (0.21) | 1.7 (0.57) |
| Texark3b | Superpave | 28518 (0.35) | 60526 (0.16) | 2.1 (0.46) |

[a]creep slope shown is inverse of deformation rate from 10,000 to 20,000 wheel passes From Table 1 it is observed that the ratio (dry/wet) of creep slopes (and rut depths) range from about 1.7 to 2.4 with an average ratio of about 2.0. Since the creep slope is the inverse of the slope of the deformation curve, the data suggest the rutting rate for wet specimens is about twice that of dry specimens in the wheel tracking test.

Conclusion

Based on the data collected thus far, there appears to be a difference in the rutting characteristics of an HMAC specimen tested "wet" or "dry" in a Hamburg-type wheel tracking device. The data suggests that submerged specimens rut at a rate twice that of specimens tested dry.

It must be noted that the rutting rates exhibited by the specimens are very small, due in part to the nature of the mixes and to the fact that the tests were performed at 25° C. (77° F.). None of the mixes tested here would qualify as being "rutting susceptible" under common Hamburg-type specifications. It is importance of this study, however, is the comparison between companion specimens.

This data could prove significant in terms of laboratory testing parameters for estimating the rutting and stripping susceptibility of mixes using Hamburg-type wheel tracking devices. A purely "rutting-based" evaluation could potentially require a different test setup than that for a "stripping-based" evaluation. Another possibility is that there could be verifiable ratio of rutting rate between wet and dry specimens, leading to a "correction factor" for rutting of a submerged specimen.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the example and descriptions set forth herein but rather that the claims be construed as encompassing all the features of patentable novelty which reside in the present invention, including all features which would be treated as equivalents thereof by those skilled in the art to which this invention pertains.

We claim:

1. An apparatus for analyzing a first sample and a second sample which apparatus comprises:

(a) a frame;

(b) a first sample container supported by the frame designed to maintain the first sample in a dry state;

(c) a second container supported by the frame designed to contain the second sample either in a dry state or submerged in a liquid;

(d) a reciprocating member supported by the frame having a first contacting surface for contacting the first sample, and a second contacting surface for contacting the second sample, wherein the first and second samples are simultaneously contacted; and (e) a sensor for measuring the penetration of the first contacting surface into the first sample, and the penetration of the second contacting surface into the second sample.

2. The apparatus of claim 1 further comprising:

(f) a data acquisition device.

3. The apparatus of claim 1 further comprising:

(g) a temperature controller for maintaining the first sample and the second sample at a constant temperature.

4. The apparatus of claim 3 further comprising:

(h) a cover supported by the frame which encloses the sample containers.

5. The apparatus of claim 1 wherein the reciprocating member is a wheel.

6. A method for analyzing a sample which method comprises:

(a) placing a first sample into a first sample container and maintaining the first sample dry;

(b) placing a second sample into a second sample container and maintaining the second sample dry or submerged in a liquid;

(c) simultaneously contacting the first and second test samples with a reciprocating member;

(d) measuring the depth at which the reciprocating member penetrates the first and second samples.

7. The method of claim 6 further comprising:

(e) weighting the reciprocating member with a load.

8. The method of claim 7 wherein the load is between about 55 pounds to about 250 pounds.

9. The method of claim 6 wherein the first sample and the second sample are contacted with the reciprocating member for between about 5000 cycles and about 80000 cycles.

10. The method of claim 6 wherein the first sample and the second sample are contacted with the reciprocating member at a rate of between about 50 cycles/hour and about 4000 cycles/hour.

11. The method of claim 6, further comprising:

(e) determining a ratio of the depth at which the reciprocating member penetrates first sample to the depth at which the reciprocating member penetrates the second sample.

* * * * *